United States Patent
Edwards et al.

(10) Patent No.: US 12,282,035 B2
(45) Date of Patent: Apr. 22, 2025

(54) AUTOMATED LABORATORY SYSTEM RESOURCE ALLOCATION AND UTILIZATION

(71) Applicant: Leica Biosystems Melbourne Pty Ltd, Mt. Waverly (AU)

(72) Inventors: Steven John Edwards, Sandringham (AU); Andreas Ernst, Glen Waverly (AU)

(73) Assignee: Leica Biosystems Melbourne Pty Ltd, Mt. Waverly (AU)

( * ) Notice: Subject to any disclaimer, the term of this patent is extended or adjusted under 35 U.S.C. 154(b) by 815 days.

(21) Appl. No.: 17/414,888

(22) PCT Filed: Dec. 19, 2019

(86) PCT No.: PCT/AU2019/051410
§ 371 (c)(1),
(2) Date: Jun. 16, 2021

(87) PCT Pub. No.: WO2020/124157
PCT Pub. Date: Jun. 25, 2020

(65) Prior Publication Data
US 2022/0057418 A1    Feb. 24, 2022

(30) Foreign Application Priority Data

Dec. 20, 2018    (AU) .................. 2018904862

(51) Int. Cl.
*G01N 1/00*    (2006.01)
*G01N 1/31*    (2006.01)
*G01N 35/00*    (2006.01)

(52) U.S. Cl.
CPC ......... *G01N 35/0092* (2013.01); *G01N 1/312* (2013.01); *G01N 2035/0094* (2013.01)

(58) Field of Classification Search
None
See application file for complete search history.

(56) References Cited

U.S. PATENT DOCUMENTS

| | | | |
|---|---|---|---|
| 6,458,598 B1 | 10/2002 | Huang | |
| 8,734,735 B2 | 5/2014 | Williamson, IV et al. | |

(Continued)

FOREIGN PATENT DOCUMENTS

| | | |
|---|---|---|
| EP | 2 259 042 A2 | 12/2010 |
| WO | WO 1995/008774 A2 | 3/1995 |

OTHER PUBLICATIONS

Extended European Search Report and Written Opinion dated Jul. 19, 2022, for Application No. 19898420.5, 9 pages.

(Continued)

*Primary Examiner* — Jyoti Nagpaul
(74) *Attorney, Agent, or Firm* — Frost Brown Todd LLP

(57) ABSTRACT

A system and method for allocating processing resources in an automated laboratory system configured with processing units at which one or more activities are performed using one or more processing resources are provided. A scheduler component received receiving at least one order requiring the execution of one or more protocols on the automated laboratory system. The scheduler generates one or more optimisation problem instances and utilizes the optimisation problem instances to generate the schedule of activities for the automated laboratory system. The scheduler causes the implementation of the generating schedule such that the activities can be performed according to desired protocol steps.

8 Claims, 4 Drawing Sheets

(56) References Cited

U.S. PATENT DOCUMENTS

2014/0129172 A1    5/2014  Eberhardt et al.
2018/0080949 A1*  3/2018  Jost ................. G06Q 10/06316

OTHER PUBLICATIONS

International Search Report and Written Opinion dated Mar. 16, 2020, for International Application No. PCT/AU2019/051410, 12 pages.
European Communication dated Dec. 3, 2024, for Application No. 19898420.5, 6 pages.

* cited by examiner

AUTOMATED LABORATORY SYSTEM RESOURCE ALLOCATION AND UTILIZATION

TECHNICAL FIELD

The present invention relates generally to methods and systems for generating a schedule of activities for an automated laboratory system including one or more banks of processing units at which activities are performed using various processing resources. The invention is of particular, but not exclusive, application to intriguing tissue samples disposed on slides using a plurality of reagents to stain the tissue samples.

BACKGROUND OF INVENTION

Automatic laboratory systems adapted to treat one or more biological samples disposed on substrates are configured to perform various activities on the samples defined by protocol(s). Each protocol step has a fixed duration and requires a certain amount of one or more processing resources such as instrument resources (e.g. transport systems for sample holders and reaction vessels, robotic arms with pipettes to transfer and dose the samples and/or reagent liquids, fluid mixers, incubator positions, photo detector positions, and the like). And consumable resources (e.g. reagents, disposable fluid carriers such as tubes, reaction vessels, multi-well plates or other fluid carriers for sample fluid and reagents, disposable pipette tips and many more).

It can happen that multiple samples are required to be processed in parallel to increase throughput or reduce a time-to-result. Accordingly, multiple protocols are required to run fully or partially in parallel and share some of the resources, requiring a pattern of resource activities on the laboratory system that can be very complex. The development and operation of a schedule of operations for automated laboratory systems that deals with complex and competing demands for resources, whilst minimising a time-to-result and increasing throughput is an important part of modern automated laboratory systems that requires continual improvement.

It would be desirable to provide a method and system for generating a schedule of activities for an automated laboratory system that ameliorates and/or overcomes one or more problems or inconveniences of the prior art.

The discussion of documents, acts, materials, devices, articles and the like is included in this specification solely for the purpose of providing a context for the present invention. It is not suggested or represented that any of these matters formed part of the prior art base or were common general knowledge in the field relevant to the present invention as it is existed before the priority date of each claim of this application.

SUMMARY OF INVENTION

One aspect of the invention provides a laboratory network, including: (a) an automated laboratory system, including one or more banks of processing units at which one or more activities are performed using one or more processing resources; and (b) a scheduler configured to generate a schedule of activities for the automated laboratory system by: receiving at least one order, each order requiring the execution of one or more protocols on the automated laboratory system generating one or more optimisation problem instances using one or more resource descriptions characterising the processing resources; one or more protocol descriptions each defining a sequence of protocol steps to be carried out by the automated laboratory equipment, where each protocol step has a known duration and requires a certain amount of one or more of the processing resources during the known term, and initial precedence constraints having a weight corresponding to the time to be observed between the time after the start of a predecessor protocol step and the start of a next protocol step; and an optimisation goal; providing the optimisation problem instances to a constraint optimisation solver; processing the optimisation problem instances by the constraint optimisation solver to generate the schedule of activities for the automated laboratory system, wherein when more than one instance of a same protocol is to be carried out on processing units forming part of a same bank, the constraint optimisation solver is configured to introduce additional precedence constraints having a zero weighting between identical processing steps in separate protocol instances, thereby indicating that start times between identical processing steps can be swapped, to find schedules where the additional precedence constraints are held and all initial precedence constraints are still valid; and scheduling the processing resources such that the activities can be performed according to desired protocol steps.

Another aspect of the present invention provides a method for generating a schedule of activities for an automated laboratory system, the automated laboratory system including one or more banks of processing units at which one or more activities are performed using one or more processing resources, the method including: receiving at least one order, each order requiring the execution of one or more protocols on the automated laboratory system generating one or more optimisation problem instances using one or more resource descriptions characterising the processing resources; one or more protocol descriptions each defining a sequence of protocol steps to be carried out by the automated laboratory equipment, where each protocol step has a known duration and requires a certain amount of one or more of the processing resources during the known term, and initial precedence constraints having a weight corresponding to the time to be observed between the time after the start of a predecessor protocol step and the start of a next protocol step; and an optimisation goal; providing the optimisation problem instances to a constraint optimisation solver; processing the optimisation problem instances by the constraint optimisation solver to generate the schedule of activities for the automated laboratory system, wherein when more than one instance of a same protocol is to be carried out on processing units forming part of a same bank, the constraint optimisation solver is configured to introduce additional precedence constraints having a zero weighting between identical processing steps in separate protocol instances, thereby indicating that start times between identical processing steps can be swapped, to find schedules where the additional precedence constraints are held and all initial precedence constraints are still valid; and scheduling the processing resources such that the activities can be performed according to desired protocol steps.

Other features of one or embodiments of the invention will be apparent in light of the description of the disclosure embodied herein.

BRIEF DESCRIPTION OF DRAWINGS

The following detailed description of specific embodiments of the present disclosure can be best understood when read in conjunction with the following drawings, wherein like structure is indicated with like reference numerals and in which.

DETAILED DESCRIPTION

Figure 1:
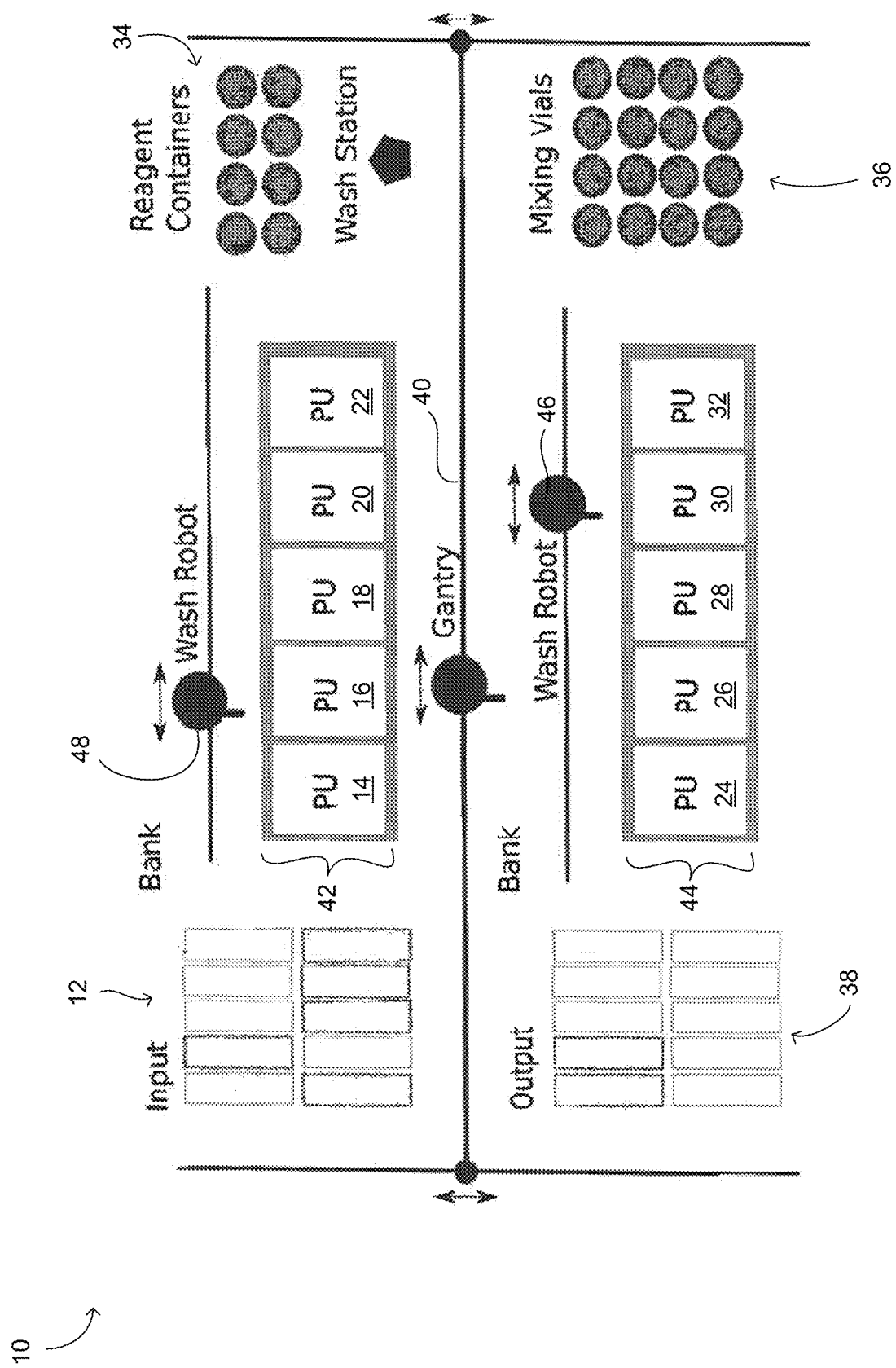
FIG. 1 is a schematic diagram of one embodiment of an automated laboratory system.

Referring now to FIG. 1, there is shown generally an automated laboratory system 10 including an input tray 12, processing units 14 to 32, reagent containers 34, mixing vials 36 and an output tray 38. In use, laboratory technicians load slides into the input drawer 12. A gantry 40 transfers slides from the input tray 12 to a selected one of the processing units 14 to 32. The processing units are situated or grouped in two separate banks 42 and 44. It will be appreciated that in other embodiments, both the number of banks and the number of processing units in each bank may vary.

Once a slide is positioned on a processing unit 14 to 32, the automated laboratory system is configured to complete a set of tasks, process the slide according to a specified protocol. The primary focus of these tasks is to transfer reagents from the reagent containers 34 to the slide in a specified order and to ensure that the reagents and sample located on the slide have the correct chemical reactions, by heating and cooling the slides as well as by using vacuums to continuously move the reagents over the sample. Other tasks that may be required to be completed by the system include but are not limited to mixing new reagents from component reagents in the mixing vials 36, washing the liquid handling probes of wash robots 46 and 48 and the gantry 40, as well as cleaning the processing units 14 to 32 and the mixing vials 36 after use. Once the slide has finished processing, the gantry 40 transfers into the output drawer 38 where the technician can remove it from the system.

The above described automated laboratory system is exemplary only, and in other embodiments, may include different types of numbers of transport systems for sample holders and reaction vessels, robotic arms and pipettes to transfer and dose sample and/or reagent liquids, fluid mixers, incubated positions, photo detector positions and other instrument resources. Similarly, in other embodiments, the automated laboratory system may include different types and numbers of consumable resources such as reagents, disposable fluid carriers such as tubes, reaction vessels, multi-well plates or other fluid carriers for sample fluids and reagents, disposable pipettes and the like.

Figure 3:
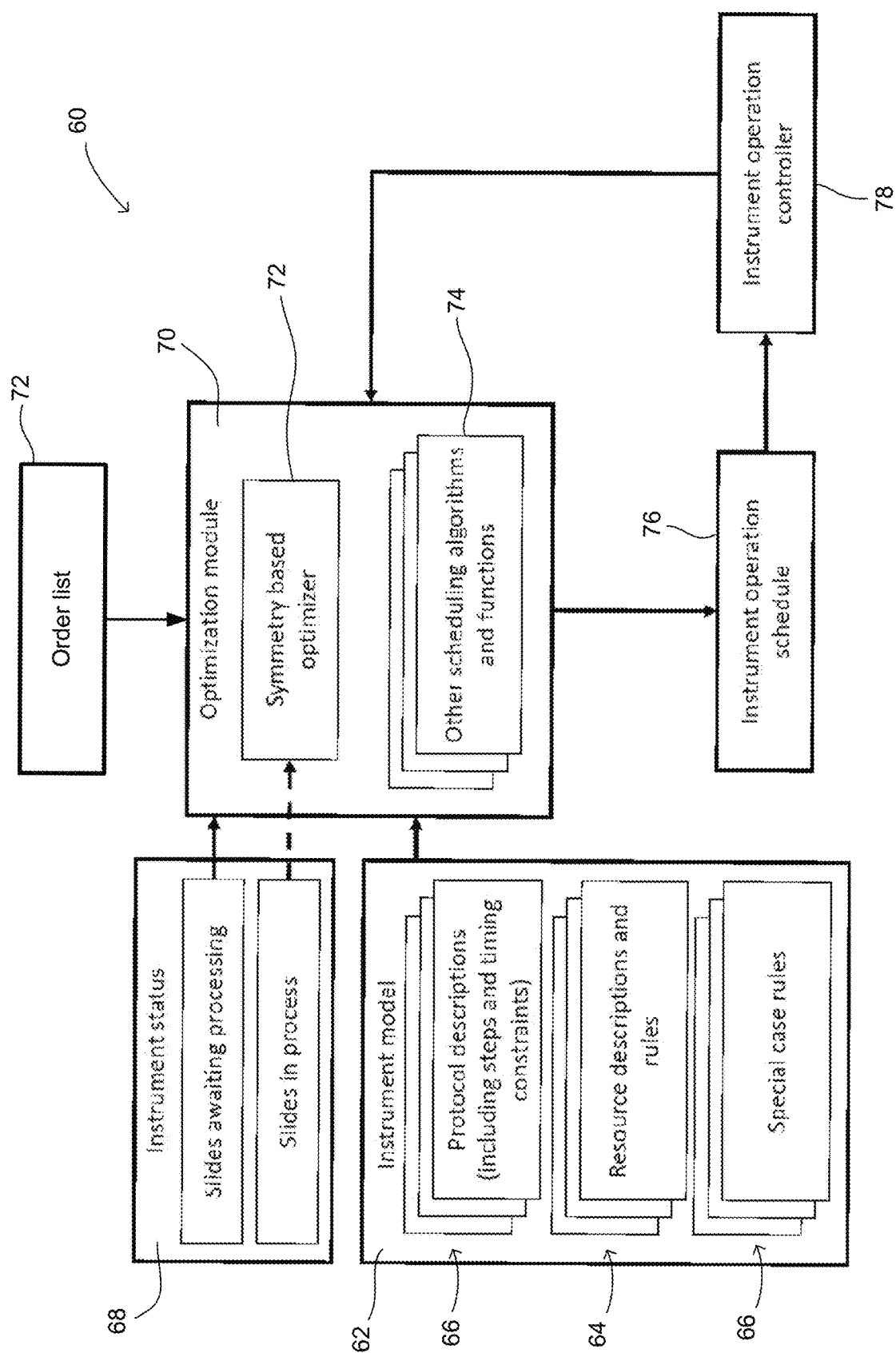

The sequence of operations performed by the automated laboratory system 10 shown in FIG. 1 is determined by a scheduler (shown in FIG. 3). The scheduler aims to schedule the resources (e.g. robots, vacuums, heating/cooling apparatus and the like) of the automated laboratory system 10 such that multiple samples can be processed in parallel in an efficient manner so that the time required to perform all processing operations is minimised and no protocol rules are violated.

Figure 2:
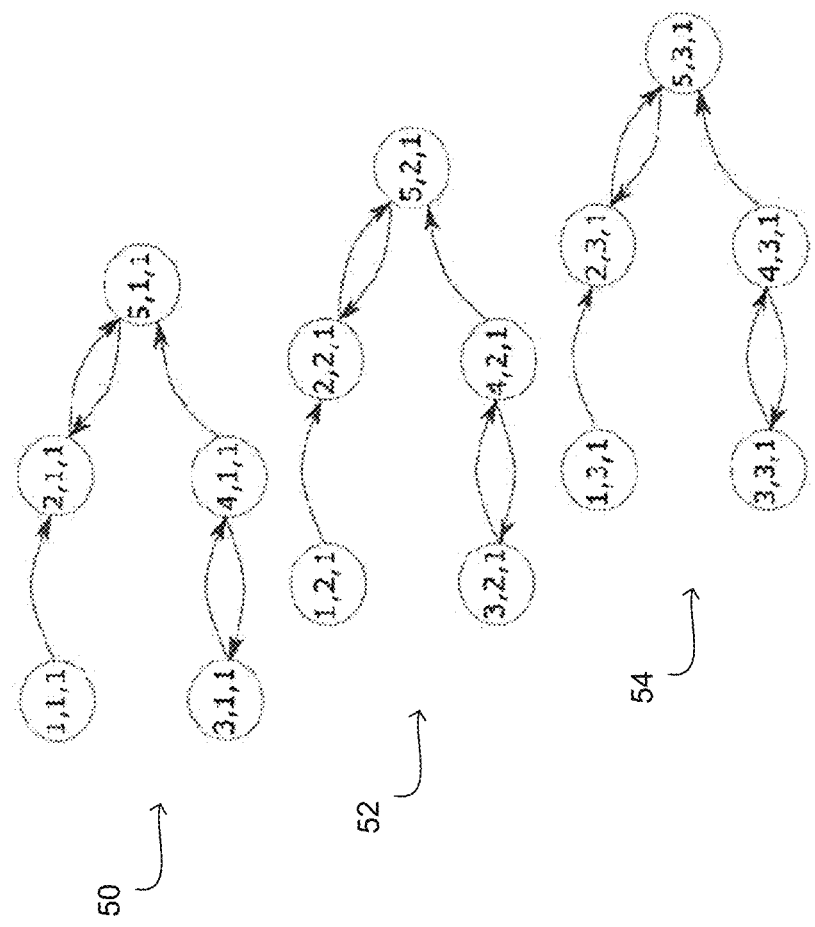

Representative tasks or activities that must be performed by the automated laboratory system 10 are depicted in FIG. 2. Three different protocols 50, 52 and 54 are shown symbolically. The tasks or activities that the automated laboratory system 10 must complete are represented by nodes (vertices) and the timing requirements between pairs of tasks are represented by weighted arcs (arrows). Each activity has a fixed duration and requires a certain amount of each resource for the duration of the activity. Activities cannot be interrupted. Each arc has an associated weight, which states the amount of time after the start of the predecessor activity (at the arc's tail) that the system must weigh before starting the successor activity (at the arc's tip). These weights can be negative, which then specifies a maximum amount of time between the start times. The protocols depicted in FIG. 2 are optimised and then implemented on the automated laboratory system 10 by a scheduler 60 depicted in FIG. 3. A scheduler 60 includes a model 62 of the automated laboratory system 10. The model includes one or more resource descriptions and rules 64 and one or more protocol descriptions 66 each defining a sequence of protocol steps to be carried out by the automated laboratory system 10, where each protocol step has a known duration and requires a certain amount of one or more of the processing resources during the known duration. The instrument will also include special case rules 66 defining modifications to the protocol description 66 and/or the resource descriptions and rules 64 that may be implemented in particular cases.

The scheduler 60 also includes an instrument status module 68 tracking the slides in process within the automated laboratory system 10 including those waiting to be processed in the input tray 12 and those currently being processed at the processing units 14 to 32.

The scheduler 60 further includes a constraint optimisation module 70. The scheduler 60 can receive an order list 72 including at least one order as part of the schedule generation process. Each order can involve the execution of one or more protocols. For example, an order list can define a plurality of assays to be carried out by the automated laboratory system 10 on a sample or batch of samples. The protocol description 64 can include a definition of one or more protocol steps to be carried out by the automated laboratory equipment 10 and one more constraints to be observed when carrying out the protocol steps on the automated laboratory equipment 10.

Figure 4:
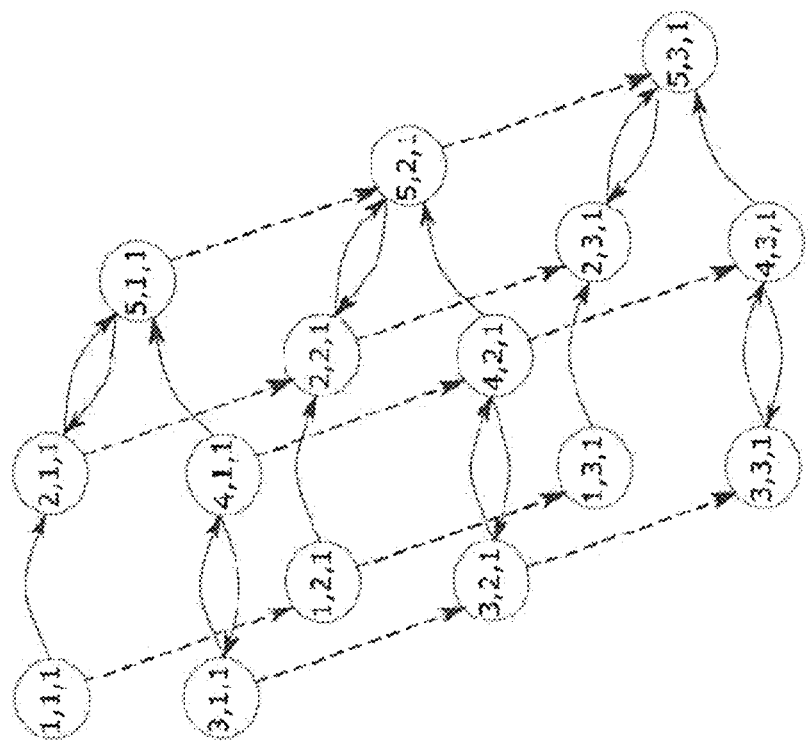
FIGS. 2 to 4 are graphical representations of the scheduling of various tasks or activities carried out during configuration of the automated laboratory system shown in FIG. 1.

In addition to conventional scheduling algorithms and functions 74, the optimisation module 70 includes a symmetry based optimiser 72 which, when more than one instance of a same protocol is to be carried out on processing units forming part of a same bank, introduces additional precedence constraints having a zero weighting between identical processing steps in separate protocol instances, thereby indicating that start times between identical processing steps can be swapped, to find schedules where the additional precedence constraints are held and all initial precedence constraints are still valid. These additional precedent constraints are depicted as dotted lines in FIG. 4. In other words, the symmetry based optimiser 72 enables the optimisation 70 to consider optimisation solutions in which it is possible to swap start times between identical activities to find schedules where those additional precedence constraints would have been held and all other constraints still valid.

These additional precedence constraints reduce the search space of the optimisation problem processed by the optimisation module 70, that is, force scheduling algorithms to look in better areas such that better solutions can be found faster than in conventional schedulers. After introduction of the additional symmetry of ranking constraints into the conventional optimisation problem solving steps involving consideration of initial precedence constraints, an optimised instrument operation schedule 76 is generated by the optimisation module 70 and the schedule is then provided as an input to an instrument operation controller 78 that causes the above described functionality of the automated laboratory system 10. It will be appreciated that the automated laboratory system 10 shown in FIG. 1 and the scheduler 60 shown in FIG. 3 collectively comprise one embodiment of a laboratory network.

Figure 5:
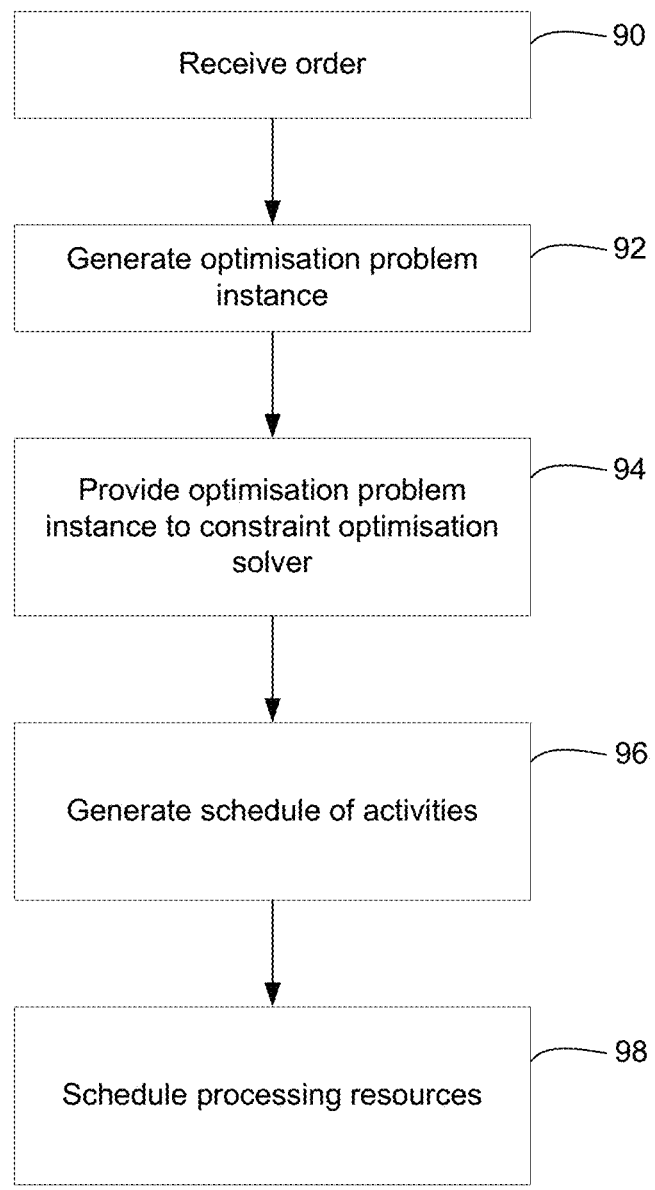
FIG. 5 is a schematic diagram of the structure of a scheduler used to control operation of the automated laboratory system shown in FIG. 1.

Operation of the scheduler 60 is depicted in FIG. 5. At step 90, the scheduler receives at least one order, each order requiring the execution of one or more protocols on the automated laboratory system 10.

The scheduler 60 then generates one or more optimisation problem instances using one or more resource descriptions characterising that processing resources and one or more protocol descriptions. The protocol descriptions define a sequence of protocol steps to be carried out by the automated laboratory, where each protocol step has a fixed duration and requires a certain amount of one or more of the processing resources, and initial precedence constraints having a weight corresponding to the time to be observed between the time after the start of a predecessor protocol step and the start of the next protocol step. The scheduler also uses an optimisation goal in the generation of the one or more optimisation problem instances, such as the minimisation of the total time required to perform all protocol steps without violating any precedence constraints. Other optimisation goals may be selected in other embodiments of the invention, such as increasing throughput.

At step 94, the optimisation problem instances are provided to the optimisation module 70.

At step 96, the optimisation problem instances are processed by the optimisation module 70 to generate a schedule of activities for the automated laboratory system 10. In doing so, where more than one instance of a same protocol is to be carried out on processing units form part of the same bank, the constraint optimisation solver is configured to introduce additional precedence constraints having a zero weighting between identical processing steps in separate protocol instances, thereby indicating that start times between identical processing steps can be swapped, define schedules where the additional precedence constraints are held and all initial precedence constraints are still valid.

Finally, the processing resources are scheduled such that the activities can be performed according to the desired protocol steps. It is to be understood at various alterations, additions and/or modifications may be made to the parts and steps previously described without departing from the ambit of the invention, and that in light of the above teachings, the present invention may be implemented in software, firmware and/or hardware in a variety of manners as would be understood by the skilled person.

The invention claimed is:

1. A laboratory network, including:
an automated laboratory system, including one or more banks and processing units at which one or more activities are performed using one or more processing resources;
wherein the processing units are situated or grouped into separate banks of the one or more banks; and
a scheduler configured to generate a schedule of activities for the automated laboratory system by:
i. receiving at least one order, each order requiring the execution of one or more protocols on the automated laboratory system;
ii. generating one or more optimisation problem instances using:
one or more resource descriptions characterising the processing resources;
one or more protocol descriptions each defining a sequence of protocol steps to be carried out by the automated laboratory equipment, where each protocol step has a known duration and requires a certain amount of one or more of the processing resources during the known term, and initial precedence constraints having a weight corresponding to the time to be observed between the time after the start of a predecessor protocol step and the start of a next protocol step; and
an optimisation goal;
iii. providing the one or more optimization problem instances to a constraint optimization solver;
iv. processing the one or more optimisation problem instances by the constraint optimisation solver to generate the schedule of activities for the automated laboratory system;
wherein
when more than one instance of a same protocol is to be carried out on processing units forming part of a same bank of the one or more banks, a symmetry based optimizer of the constraint optimisation solver is configured to introduce additional precedence constraints having a zero weighting between identical processing steps in separate protocol instances, thereby indicating that start times between identical processing steps can be swapped, to find schedules where the additional precedence constraints are held and all initial precedence constraints are still valid; and
v. scheduling the processing resources such that the activities can be performed according to desired protocol steps.

2. A laboratory network according to claim 1, wherein the optimisation goal is to minimise total time required to perform all protocol steps without violating any precedence constraints.

3. A laboratory network according to claim 2, wherein the processing resources include any one or more of robots, reagents, vacuums, heating apparatus, and cooling apparatus.

4. A laboratory network according to claim 1, wherein the processing resources include any one or more of robots, reagents, vacuums, heating apparatus, and cooling apparatus.

5. A method for generating a schedule of activities for an automated laboratory system, the automated laboratory system including one or more banks of processing units at which one or more activities are performed using one or more processing resources; wherein the processing units are situated or grouped into separate banks of the one or more banks; the method including:
i. receiving at least one order, each order requiring the execution of one or more protocols on the automated laboratory system;
ii. generating one or more optimisation problem instances using one or more resource descriptions characterising the processing resources; one or more protocol descriptions, each defining a sequence of protocol steps to be carried out by the automated laboratory equipment, where each protocol step has a known duration and requires a certain amount of one or more of the processing resources during the known term, and initial precedence constraints having a weight corresponding to the time to be observed between the time after the start of a predecessor protocol step and the start of a next protocol step; and an optimisation goal;

iii. providing the one of more optimisation problem instances to a constraint optimisation solver;

iv. processing the one or more optimisation problem instances by the constraint optimisation solver to generate the schedule of activities for the automated laboratory system;

wherein when more than one instance of a same protocol is to be carried out on processing units forming part of a same bank of the one or more banks, a symmetry based optimiser of the constraint optimisation solver is configured to introduce additional precedence constraints having a zero weighting between identical processing steps in separate protocol instances, thereby indicating that start times between identical processing steps can be swapped, to find schedules where the additional precedence constraints are held and all initial precedence constraints are still valid; and v. scheduling the processing resources such that the activities can be performed according to desired protocol steps.

6. A method according to claim 5, wherein the optimisation goal is to minimise total time required to perform all protocol steps without violating any precedence constraints.

7. A method according to claim 6, wherein the processing resources include any one or more of robots, reagents, vacuums, heating apparatus, and cooling apparatus.

8. A method according to claim 5, wherein the processing resources include any one or more of robots, reagents, vacuums, heating apparatus, and cooling apparatus.

* * * * *